United States Patent
Cheng et al.

(12) 
(10) Patent No.: US 6,313,314 B1
(45) Date of Patent: Nov. 6, 2001

(54) METHOD FOR PREPARING AZIDE PHOTO-INITIATORS

(75) Inventors: Kung-Lung Cheng, Hsinchu; Shu-Chen Lin, I-Lan; Woan-Shiow Tzeng, Hsinchu; Se-Tsun Hong, I-Lan, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/634,466

(22) Filed: Aug. 7, 2000

(30) Foreign Application Priority Data

Apr. 18, 2000 (TW) ................................................ 89107247

(51) Int. Cl.$^7$ ................................................ C07D 207/452
(52) U.S. Cl. ................................................ 548/549
(58) Field of Search ................................................ 548/549

(56) References Cited

U.S. PATENT DOCUMENTS 4,329,556 * 5/1982 Rubner et al. ........................ 548/549

FOREIGN PATENT DOCUMENTS

4328838 A1 * 3/1995 (DE) .

* cited by examiner

*Primary Examiner*—Fiona T. Powers
(74) *Attorney, Agent, or Firm*—Sughrue, Mion, Zinn, Macpeak & Seas, PLLC

(57) ABSTRACT

The present invention provides a novel method for the preparation of N-azidosulfonyl-arylimides, which are known as photo-initiators. At the outset, substitution reaction of 4-acetamidobenzenesulfonyl halide with $MN_3$ (M denotes hydrogen or alkaline metal) provides the corresponding azide. After de-protection to remove the actyl group, aminoarylsulfonyl azide is extracted with organic solvent, and the extract is directly used for addition reaction with maleic anhydride without concentration. Finally, end products are obtained by dehydration of the addition products using acetic anhydride/metal acetate, followed by re-crystallization in alcohol solvent. The end products are obtained in purer form and greater yield than that in conventional methods.

15 Claims, No Drawings

METHOD FOR PREPARING AZIDE PHOTO-INITIATORS

BACKGROUND OF THE INVENTION

1. Field of the Invention

The present invention generally relates to a method for the preparation of azide photo-initiators. More specifically, the present invention relates to a novel method for the preparation of N-azidosulfonyl-arylimides, which are known as photo-initiators.

2. Description of the Related Art

In the photochemical related industry, photoresist agent is the most important application. The photo image forming process makes possible the selective formation of via holes, the formation of heat and corrosion resistant protective films, dielectric films or alignment layers, in addition to the disposition of specific patterns onto substrates. Hence, photoresist agents are widely used in the manufacturing and sealing processes of ICs, and the manufacturing of LCDs and printed circuit boards.

The formula of the photoresist agent includes photo-initiators, photo-resistant agent, solvents and other additives. Among these, photo-initiators are the most expensive, the most difficult to synthesize, and have the greatest influence on the overall photosensitivity, quality and function of the agent. Generally, by exposure, the photo-initiators generate free radicals, carbene, nitrene, protons and other cations or anions to initiate the polymerization reaction and allow a subsequent series of follow-up applications.

Azide photo-initiator is one of the most important photo-initiators. By exposure to light, the Azide photo-initiator is in an excited state, in which $N_2$ is removed to form nitrene. The high reactivity of nitrene causes difficulties in polymerization, purification, usage and storage.

Various methods for the preparation of azide photo-initiators are disclosed in U.S. Pat. No. 4,329,556 (Siemens) and D.E. Pat. No. 4,328,838 (BASF). The formulation of the photoresist agent with the azide photo-initiators is disclosed in E. Pat. No. 188,205 (Merck).

In general, the method disclosed by Siemens is by reacting 4-acetamidobenzenesulfonyl chloride and $CH_2Cl_2$ solvent under the presence of the dehydrating agent N,N'-dicyclohexylcarbodiimide (DCC) to carry out the polymerization. The DCC is high-priced and moisture absorbing, hence it is hard to manage. Similarly, $CH_2Cl_2$, being regulated, is not easy to use and manufacture in Taiwan. Since the purification of product is done by chromatography, which lowers product yield to 30%, it is hard to achieve mass production.

The BASF method discloses a process in which N-phenylmaleimide, which is 10 times the price of the 4-acetamidobenzenesulfonyl chloride (310 U.S.$/kg vs. 30 U.S.$/kg), is utilized as a reactant. Moreover, as the polymerization reaction is carried out by sulfonyl chloride, problems such as waste acids and wastewater arise, making this method dirty and non-environmentally friendly.

SUMMARY OF THE INVENTION

Therefore, an object of the present invention is to provide a novel method of preparation of azide photo-initiators.

The present invention achieves the above-indicated objects by providing a novel polymerization process using N-azidosulfonyl-arylimides. According to the invention, substitution reaction of 4-acetamidobenzenesulfonyl halide with $MN_3$ (M denotes hydrogen or alkaline metal) provides the corresponding azide. After de-protection to remove the actyl group, aminoarylsulfonyl azide is extracted with an organic solvent, and the extract is directly used for addition reaction with maleic anhydride without being concentrated. Finally, end products are obtained by dehydration of the addition products using acetic anhydride/metal acetate, followed by re-crystallization in alcohol solvent. The product yield is greater than 69% with an assay greater than 99%. Moreover, it is easy to ramp up the manufacturing to mass production, making the method useful to industry. With the addition of phenolic aldehyde resins with double-bonded and photosensitive groups, epoxy resin, polyamic resin and acrylate, etc, this method is suitable for application in the microelectronics industry.

DETAILED DESCRIPTION OF THE INVENTION

The method of the invention is now described in detail.

The azide photo-initiator used in the invention is shown as formula I:

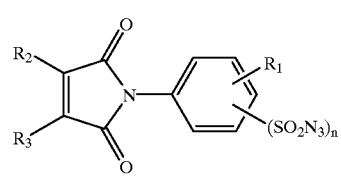

I wherein $R_1$, is hydrogen, halogen or alkyl of 1–4 carbon atoms; $R_2$ and $R_3$ are independently the same or different and each represent hydrogen, alkyl of 1–6 carbon atoms or cycloalkyl, or $R_2$ and $R_3$ combined together represent cycloalkenyl, aryl or heteroaryl; and n is 1 or 2.

The term 'aryl' or 'heteroaryl' represents groups of aromatic nature having 5 or 6 membered rings which may be selected from phenyl, biphenyl, naphthyl, pyridyl, quinoline, indole, pyrol, furan, benzofuran, thiophene, pyramidine, piperizine and imidazol etc. The rings could also include substituents, such as halogen, nitro, cyano, alkyl, alkoxyl, haloalkyl, hydroxyl, carboxyl, amido, and amino.

The method of the invention comprises the following steps:

(a) Substitution reacting compound II and $MN_3$ in a ketone solvent to obtain compound III, wherein M denotes hydrogen or alkaline metal;

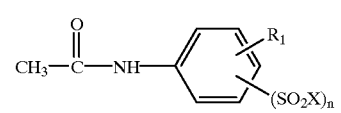

II

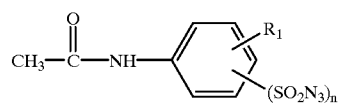

III wherein $R_1$ is hydrogen, halogen or alkyl of 1–4 carbon atoms, X is halogen, and n is 1 or 2.

(b) de-protecting the acetyl-amino of compound III under acidic conditions, adding alkaline solution to the resulting solution to adjust the pH to be larger than 7, and extracting by organic solvent to obtain compound IV;

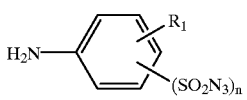

wherein $R_1$ and n are defined as above;

(c) addition reacting the resulting organic solvent extract with compound V to obtain compound VI;

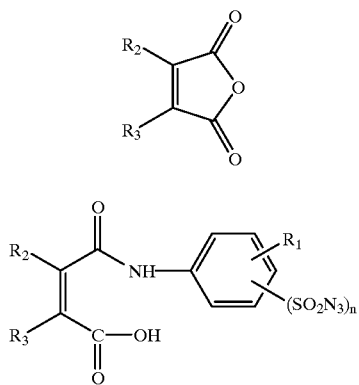

wherein $R_2$ and $R_3$ are independently the same or different and each represent hydrogen, alkyl of 1–6 carbon atoms, or cycloalkyl, or $R_2$ and $R_3$ combined together represent cycloalkenyl, aryl or heteroaryl; and (d) dehydrating compound IV with acetic anhydride and metal acetate to obtain azide photo-initiator compound I;

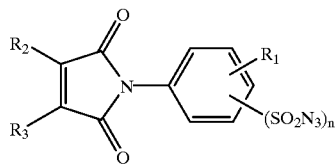

wherein $R_1$, $R_2$, $R_3$ and n are defined as above.

According to the method of the invention, step (a) is the substitution reaction of 4-Acetamidobenzenesulfonyl halide or alkanes thereof and aromatic derivatives II with MN3 in ketone solvent at temperature of 25° C. This reaction is very rapid and finishes in 5 min. TLC chromatography is then performed to ensure the reactants are completely consumed in the reaction. Next, compound III is obtained by filtration of white solid precipitate by dripping the substitution product in ice water. In this case, the ketone solvent used is ketone of 3 to 12 carbon atoms, preferably acetone. $MN_3$ is preferably $NaN_3$.

Step (b) is the de-protection of the actyl group of azide compound III under acidic conditions. This reaction is usually completed by reflux-stirring at 95° C. for 15 minutes in hydrogen halide (such as hydrogen chloride) solution, adding alkaline solution to the resultant solution to adjust the pH to be greater than 7, followed by extraction with organic solvents to obtain amino compound IV. The alkaline solution used is alkaline metal or ammonium hydroxide solution, preferably ammonium hydroxide solution. The organic solvents suitable for use in the extraction include esters, ketones, ethers, alcohols, aliphatics, aromatic solvents etc, preferably ethyl acetate. The obtained organic solvent extract is then used in the next addition reaction. However, the extract may be concentrated, dried and weighed in order to calculate the accurate product yield of this step.

Step (c) is the addition reaction of the obtained organic solvent extract with maleic anhydride or alkanes thereof and aromatic derivative V to obtain amide compound VI. This addition reaction normally takes place at a temperature of 35–40° C. for 6.5–7 hours. A slightly yellowish and green product is obtained after filtration and drying.

The same organic solvent is used in the above two reaction steps (b and c), thereby decreasing the number of steps for concentration work-up. This reaction is simple and easy to conduct, which is one of the features of the invention.

Dehydration of amide compound VI with acetic anhydride and metal acetate in step (d) is carried out for about 7 hours at room temperature. The obtained product is filtrated, and the filtrated solution can be neutralized by saturated $NaHCO_3$ solution. The two products are then combined and washed with pure water, and dried to obtain a white solid precipitate. This solid precipitate is re-crystallized with alcohol to obtain azide photo-initiator compound I. The metal acetates are alkaline metal acetates, preferably sodium acetate. The alcohol suitable for use in the re-crystallization is alcohol of 1 to 12 carbon atoms, preferably methanol.

The process of the invention is conducted in a homogeneous reflux reaction under normal pressure. The reaction temperature is controlled at 0–120° C., preferably 25–95° C. In addition, it is not necessary to have light shielding or yellow light surroundings and equipment. The 4-step overall product yield is 69% with an assay of 99%, and it is easy ramp up the production to industrial levels.

The azide photo-initiators of the invention can be used in photoresist agents such as photo-sensitive or cross-linkable phenolic aldehyde resins, epoxy resins, polyamic resins, acrylic resins, silicon or polyvinyl. The amount added is 0.01–20 wt %, preferably 1–5 wt %. Moreover, the photo-initiators of the invention can be utilized as protective layers, dielectric films, insulation layers, electrical adherents, sealing material of ICs, addition and insulation layers for the substrates of printed circuit boards, and alignment layers of LCDs.

Without intending to limit it in any manner, the present invention will be further illustrated by the following examples.

EXAMPLE 1

4-Acetylaminobenzenesulfonyl Azide 10 g (0.043 mole) of solid 4-Acetamidobenzenesulfonyl chloride and 90 ml of acetone were added into a 250 ml, double-neck reaction flask with magnetic stirrers and a condenser. At room temperature (25° C.), 3.34 g (0.0516 mole of solid dissolved in 20 ml of $H_2O$)of $NaN_3$ solution was dripped and stirred for about 5 min to 18 hours. TLC chromatography was then carried out to ensure that the initial reactants were consumed completely in the reaction.

The obtained solution was dripped into 250 ml of ice water and then stirred vigorously for at least 1 hour. At that point, a white solid precipitate was produced and then filtered with filtration paper. By washing the filtrate with ice water, a white solid product was obtained. After drying, the final product was completed. The product yield is shown in Table 1. Note that the product yield of the reaction at the low temperature of −4° C. was not improved.

The analytical data of the product is as follows:

Melting point: 108–110° C. ;Reference data: 113° C. (Re-crystallized with toluene solvent)

$^1$H NMR (CDCl$_3$, 200MHz): δ2.26 (3H, s), 7.78–7.91 (4H, m), 8.33 (1H, br)

$^{13}$C NMR (CDCl$_3$, 50MHz): δ24.7 (q), 119.6 (d, 2C), 128.9 (d, 2C), 132.3 (s), 144.0 (s), 169.3 (s)

IR (KBr): 3302–3060, 2130, 1676, 1586, 1365, 1178 cm$^{-1}$LC/MS (m/z): 239 (M$^+$−1)

TABLE 1

| No. | Reaction time | Product yield (%) |
|---|---|---|
| 1-1[a] | 18 hr | 73.2 |
| 1-2[a] | 7 hr | 77.2 |
| 1-3[a] | 5 hr | 85.6 |
| 1-4[a] | 5 min | 79.0 |
| 1-5[a] | 5 min | 85.2 |
| 1-6[b] | 1 hr | 83.9 |

※[a]: reaction temperature : 25° C.
[b]: reaction temperature : −4° C.

EXAMPLE 2

4-Aminobenzenesulfonyl Azide 8.175 g of the obtained 4-aminobenzenesulfonyl azide, 6.2–18 ml of 12N HCl$_{(aq)}$ and an equal amount (6.2–18 ml) of H$_2$O were placed into a 100 ml, double-neck reaction flask with magnetic stirrers and a condenser. At temperature of 95° C., the solution was refluxed for 15 min. After it was returned to room temperature, 30% of NH$_4$OH solution was added to adjust the value of pH to be greater than 7.

The solution was extracted with ethyl acetate or CH$_2$Cl$_2$ (100 ml×3 times), and the organic layers were combined. After drying with anhydrous sodium sulfate, filtration and concentration with a rotary evaporator, a reddish brown product was obtained. The ethyl acetate extracted solution can be used in the next reaction without being concentrated.

Extraction with ethyl acetate is not only low in toxicity, it also generates better product yield than using CH$_2$Cl$_2$, as shown in Table 2-1. Table 2-2 illustrates that the addition of different amounts of HCl$_{(ag)}$ also affects the product yield.

The analytic data of product is as follows:

Melting point : 35–39° C.

$^1$H NMR (CDCl$_3$, 200 MHz): δ4.47 (2H, br), 6.72 (2H, dd, J=8.7, 2.2 Hz), 7.70 (2H, dd, J=8.7, 2.2 Hz)

$^3$C NMR (CDCl$_3$, 50 MHz): δ6114.0 (d, 2C), 129.9 (d, 2C), 133.1 (s), 152.6 (s)

IR (neat): 3499, 3402, 2133, 1596, 1366, 1169 cm$^{-1}$LC/MS (m/z): 197 (M$^+$−1)

TABLE 2-1

| No. | Reacting solvent | Product yield (%) |
|---|---|---|
| 2-1 | CH$_2$Cl$_2$ | 76.69 |
| 2-2 | CH$_2$Cl$_2$ | 90.31 |
| 2-3 | Ethyl acetate | 89.94 |
| 2-4 | Ethyl acetate | 95.63 |
| 2-5 | Ethyl acetate | 90.53 |

TABLE 2-2

| No. | amount of HCl(mole)added | Product yield (%) |
|---|---|---|
| 2-4 | 5.8 | 95.63 |
| 2-6 | 5.0 | 90.53 |
| 2-7 | 2 | 89.56 |

※Reaction condition : Temperature 95° C. ; reaction time: 15 min

EXAMPLE 3

N-(4-Azidosulfonylphenyl)-maleic acid monoamide 1.547 g (0.016 mole)of Maleic anhydride and 3.5 ml of reacting solvent (NMP, THF, ether or ethyl acetate) were added into a 50 ml, double-neck reaction flask. At room temperature of 25° C., 2.604 g (0.013 mole) of the obtained 4-aminobenzenesulfonyl azide and 3.5 ml of reacting solvent ethyl acetate were added by dripping.

At temperature of 35° C., a yellowish solid was precipitated gradually, and a suspension solution was formed. The suspension solution was stirred for about 6.5 hours. The product was filtrated and washed with the reacting solvent to obtain yellowish product. The final product was obtained after drying.

As shown in Table 3, different ratios of reactants, reaction conditions and reacting solvents all affected the product yield. The best ratio of reactants was 1:1.2, the reaction temperature was 35° C., and the reaction time was 6.5 hours. The best reacting solvent was ethyl acetate.

Low toxic ethyl acetate was used as the reacting solvent and the product yield of the present invention was considerably better than that in the prior art. The invention not only uses ethyl acetate to extract, but also to carry out the addition reaction with the obtained ethyl acetate extracted solution and maleic anhydride. This has results in a reduction of concentrate work-up steps and makes the invention an easy and simple process.

The analytic data of product is as follows:

Melting point: 167–169° C.

$^{13}$H NMR (CD$_3$COCD$_3$+CD$_3$SOCD$_3$, 200 MHz): δ66.34 (1H, d, J=12.1 Hz), 6.58 (1H, d, J=12.1 Hz), 7.95–8.08 (4H, m), 10.94 (1H, br)

$^{13}$C NMR (CD$_3$COCD$_3$+CD$_3$SOCD$_3$, 50 MHz): δ6120.5 (d, 2C), 129.6 (d, 2C), 131.3 (d), 132.5 (s), 132.9 (d), 146.0 (s), 165.2 (s), 167.4 (s)

IR (KBr): 3690, 3302–3020, 2137, 1701, 1637, 1610, 1595, 1369, 1175 cm$^{-1}$

LC/MS (m/z): 295 (M$^+$1)

TABLE 3

| No. | The ration of reactants and reaction condition | Reacting solvent | Product yield (%) |
|---|---|---|---|
| 3-1 | 1:1.02 | NMP | 50.94 |
| 3-2 | 1:1 | THF | 33.57 |
| 3-3 | 1:1 | Diethyl Ether | — |
| 3-4 | 1:1.1 (35° C., 6.5 hr) | EA | 93.27 |
| 3-5 | 1:1.2 (35° C., 6 hr) | EA | 97.84 |
| 3-6 | 1:1.2 (35° C., 7 hr) | EA | 97.12 |
| 3-7 | 1:1.2 (40° C., 6.5 hr) | EA | 93.79 |

EXAMPLE 4

N-(4-Azidosulfonylphenyl)-maleinimide 2.806 g (0.01 mole) of the obtained N-(4-azidosulfonylphenyl)-maleic acid monoamide, 0.162 g (0.002 mole) of sodium acetate and 8.065 g (0.08 mole) of anhydride acetate were added in a 50 ml reaction flask and stirred for about 7 hours at room temperature of 25° C.

During the reaction, the solution turned into clear liquid gradually and then turned into a reddish brown suspension solution. A white solid was precipitated. A white solid product was obtained after filtering the precipitate. The filtrated solution was then neutralized with saturated $NaHCO_3$ solution, and the pH value was adjusted to be greater than 7 in order to obtain another portion of precipitate.

The two products were combined and washed with pure water, then dried to obtain a white solid product. Then the product was re-crystallized purified with alcohol. The product yield is shown in Table 4. The assay of the product was greater than 99%.

The analytical data of product is as follows:

Melting point: 119–121° C., Reference data: 120° C.

$^1$H NMR ($CDCl_3$, 200 MHz): δ6 6.91 (2H, H) , 7.72 (2H, dd, J=8.7, 2.0 Hz), 8.02 (2H, dd, J=8.7, 2.0 Hz)

$^{13}$C NMR ($CDCl_3$, 50 MHz): δ6125.8 (d, 2C), 128.5 (d, 2C), 134.6 (d, 2C), 136.7 (s), 137.2 (s), 168.4 (s, 2C)

UV λmax (MeOH) : 286 nm (ε=$1.92 \times 10^4$)

IR (KBr) : 3103, 2132, 1734, 1595, 1363, 1178 $cm^{-1}$

LC/MS (m/z) : 277 ($M^+$−1)

TABLE 4

| No. | Amount of anhydride acetate | Reaction time | Product yield (%) |
|---|---|---|---|
| 4-1[a,b] | 4 eq | — | — |
| 4-2[a] | 8 eq | 7 hr | 87.12 |
| 4-3[a] | 8 eq | 7 hr | 87.12 |
| 4-4[a] | 8 eq | 5 hr | 86.2 |

[a]: Amount of sodium acetate: 0.2 equivaient ratio (based on N-(4-azidosulfonyl-phenyl)-maleic acid monoamide)
[b]: The solution was too concentrated to go any further.

According to these embodiments of the present invention, a novel method for preparing azide photo-initiators, with a product yield greater than 69% and an assay greater than 99% is achieved.

While the invention has been described by way of example and in terms of the preferred embodiment, it is to be understood that the invention is not limited to the disclosed embodiments. On the contrary, it is intended to cover various modifications and similar arrangements as would be apparent to those skilled in the art. Similarly, any process steps described herein may be interchangeable with other steps in order to achieve the same result. Therefore, the scope of the appended claims should be accorded the broadest interpretation so as to encompass all such modifications and similar arrangements, which is defined by the following claims and their equivalents.

What is claimed is:

1. A method for the preparation of azide photo-initiators comprising:

a. substitution reacting compound II and $MN_3$ in a ketone solvent to obtain compound III, wherein M is hydrogen or alkaline metal and compound II and compound III are as follows:

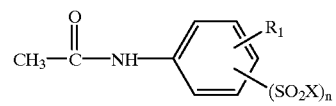

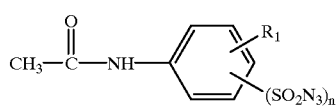

wherein $R_1$ is hydrogen, halogen or alkyl of 1–4 carbon atoms, X is halogen, and n is 1 or 2.

b. de-protecting the acetyl-amino of compound III in acid condition, adding alkaline solution to the resulting solution to adjust the pH to be greater than 7, and extracting by organic solvent to obtain compound IV:

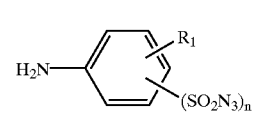

c. addition reacting the resulting organic solvent extract with compound V to obtain compound VI:

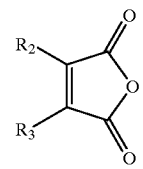

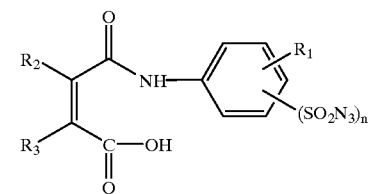

wherein $R_2$ and $R_3$ are independently the same or different and each represent hydrogen, alkyls of 1–6 carbon atoms, or cycloalkyl, or $R_2$ and $R_3$ combined together represent cycloalkenyl, aryl or heteroaryl; and d. dehydrating compound IV by acetic anhydride and metal acetate to obtain azide photo-initiator compound I;

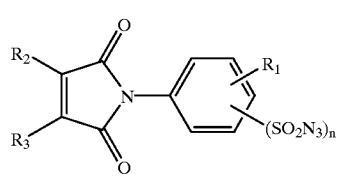

wherein $R_1$, $R_2$, $R_3$ and n are defined as above.

2. The method according to claim 1, wherein said ketone solvent is ketone solvent of 3–12 carbon atoms.

3. The method according to claim 1, wherein the de-protecting step (b) comprises adding hydrogen halide solution under acidic conditions.

4. The method according to claim 1, wherein said alkaline solution is alkaline metal or ammonium hydroxide solution.

5. The method according to claim 1, wherein said organic solvents are selected from the group consisting of esters, ketones, ethers, alcohols, aromatic solvents and combinations thereof.

6. The method according to claim 1, wherein said metal acetate is alkaline metal acetate.

7. The method according to claim 1, wherein the reaction temperature in steps a, b, c and d is between 0~120° C.

8. The method according to claim 1, wherein steps (d) further comprises re-crystallizing the product by alcohol solvents of 1–12 carbon atoms.

9. The method according to claim 1, wherein $R_1$ is hydrogen and n is 1.

10. The method according to claim 1, wherein $R_2$, $R_3$ are hydrogen.

11. A method for the preparation of azide photo-initiator comprising:
   a. substitution reacting compound II and $NaN_3$ in acetone solvent to obtain compound III,

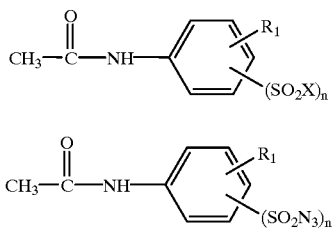

wherein $R_1$ is hydrogen, X is halogen, and n is 1;

b. de-protecting compound III in hydrogen chloride solution, adding ammonium hydroxide solution to the resulting solution to adjust the pH to be greater than 7, and extracting by ethyl acetate to obtain compound IV:

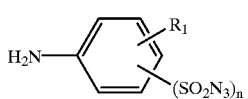

c. addition reacting the resulting ethyl acetate solvent extract with compound V to obtain compound VI:

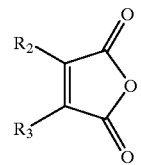

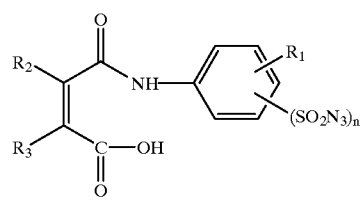

wherein $R_2$ and $R_3$ are hydrogen; and d. dehydrating compound IV by acetic anhydride and metal acetate to obtain azide photo-initiator compound I;

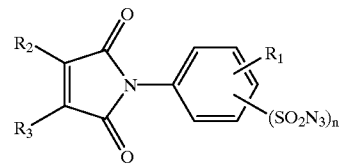

wherein $R_1$, $R_2$, $R_3$ and n are defined as above.

12. The method according to claim 11, wherein X is chlorine.

13. The method according to claim 12, wherein the reaction temperature in steps a, b, c and d is between 25~95° C.

14. The method according to claim 13, wherein step (d) further comprises re-crystallizing the resulting product by methanol.

15. The method according to claim 14, wherein the overall product yield of steps a, b, c and d is greater than 69% with an assay greater than 99%.

* * * * *